United States Patent
Han-Oh et al.

(10) Patent No.: US 10,993,619 B2
(45) Date of Patent: May 4, 2021

(54) SYSTEMS AND METHODS FOR ULTRA-WIDEBAND (UWB) RADAR DETECTION AND TRACKING OF TUMORS IN REAL-TIME

(71) Applicant: The Johns Hopkins University, Baltimore, MD (US)

(72) Inventors: Yeonju Sarah Han-Oh, Ellicott City, MD (US); Eun Oh, Ellicott City, MD (US)

(73) Assignees: The Johns Hopkins University, Baltimore, MD (US); U.S. Government in the Name of the Secretary of the Navy, Arlington, VA (US)

( * ) Notice: Subject to any disclaimer, the term of this patent is extended or adjusted under 35 U.S.C. 154(b) by 1096 days.

(21) Appl. No.: 14/891,649

(22) PCT Filed: May 30, 2014

(86) PCT No.: PCT/US2014/040369
§ 371 (c)(1),
(2) Date: Nov. 16, 2015

(87) PCT Pub. No.: WO2014/194281
PCT Pub. Date: Dec. 4, 2014

(65) Prior Publication Data
US 2016/0081618 A1 Mar. 24, 2016

Related U.S. Application Data

(60) Provisional application No. 61/829,801, filed on May 31, 2013.

(51) Int. Cl.
*A61B 5/00* (2006.01)
*A61B 5/0507* (2021.01)
(Continued)

(52) U.S. Cl.
CPC .......... *A61B 5/0036* (2018.08); *A61B 5/0059* (2013.01); *A61B 5/0082* (2013.01);
(Continued)

(58) Field of Classification Search
CPC ...... A61N 5/1049; A61B 5/0507; A61B 50/24
See application file for complete search history.

(56) References Cited

U.S. PATENT DOCUMENTS 5,907,404 A * 5/1999 Marron ............... G01J 9/02
356/489
6,064,903 A * 5/2000 Riechers ............ A61B 5/05
324/638
(Continued)

FOREIGN PATENT DOCUMENTS

JP 2012-157556 A 8/2012
WO WO 2013164827 A2 * 11/2013 ........... A61B 5/6833

OTHER PUBLICATIONS

Paulson et al. "Ultra-wideband Radar Methods and Techniques of Medical Sensing and Imaging" (2005).*
(Continued)

*Primary Examiner* — Serkan Akar
*Assistant Examiner* — Aminah Asghar
(74) *Attorney, Agent, or Firm* — Venable LLP; Henry J. Daley

(57) ABSTRACT

An ultra-wideband (UWB) radar system for non-invasive, real-time tumor tracking includes an UWB transmitter arranged to transmit radar pulses to penetrate a region of interest of a patient; an UWB receiver arranged to receive radar return pulses after being reflected by tumor tissue in the region of interest of the patient; and an UWB signal processor constructed to communicate with the UWB receiver, wherein the UWB transmitter and the UWB receiver are constructed to be arranged sufficiently far away
(Continued)

from the patient so as to avoid interfering with radiation treatment of the tumor.

14 Claims, 10 Drawing Sheets

(52) U.S. Cl.
CPC .......... *A61B 5/0507* (2013.01); *A61B 5/4836* (2013.01); *A61B 5/6844* (2013.01); *A61B 5/6887* (2013.01); *A61B 5/7217* (2013.01); *A61B 5/7257* (2013.01); *A61B 5/7271* (2013.01); *A61B 2562/04* (2013.01)

(56) References Cited

U.S. PATENT DOCUMENTS

| | | | | |
|---|---|---|---|---|
| 6,100,839 A * | 8/2000 | Heger | .................... | G01S 7/285 342/22 |
| 2006/0058606 A1 | 3/2006 | Davis et al. | | |
| 2007/0230660 A1 * | 10/2007 | Herrmann | ................ | A61N 5/10 378/65 |
| 2007/0293752 A1 * | 12/2007 | Simpkin | .............. | A61B 5/4312 600/407 |
| 2009/0209850 A1 * | 8/2009 | Tao | ........................ | A61B 5/024 600/425 |
| 2010/0054304 A1 * | 3/2010 | Barnes | ................. | H04B 1/7183 375/130 |
| 2010/0185102 A1 | 7/2010 | Saar | | |
| 2011/0115667 A1 * | 5/2011 | Feigin | ................... | G01S 7/4008 342/22 |
| 2011/0316747 A1 * | 12/2011 | Budianu | ................. | G01S 11/00 342/387 |
| 2012/0165652 A1 | 6/2012 | Dempsey | | |
| 2012/0296204 A1 | 11/2012 | Ismail et al. | | |
| 2013/0001422 A1 * | 1/2013 | Lavon | .................. | A61B 5/0205 250/338.1 |
| 2014/0336515 A1 * | 11/2014 | Tangy | .................... | A61B 5/015 600/474 |
| 2015/0301167 A1 * | 10/2015 | Sentelle | ............... | A61B 5/0205 342/22 |

OTHER PUBLICATIONS

Jianqi et al. "A New Method for Identifying the Life Parameters via Radar" (2007).*
Lazaro et al. "Simulated and experimental wavelet-based detection of breast tumor using a UWB radar", 2010, pp. 373-376 (Year: 2010).*
Woon et al. "Investigation of Methods to Extract TDOA from UWB-IR Waveforms", 2010, pp. 228-232 (Year: 2010).*
International Search Report and Written Opinion of PCT/US2014/040369.

* cited by examiner

SYSTEMS AND METHODS FOR ULTRA-WIDEBAND (UWB) RADAR DETECTION AND TRACKING OF TUMORS IN REAL-TIME

CROSS REFERENCE TO RELATED APPLICATIONS

This is a national stage application under 35 U.S.C. § 371 of PCT/US2014/040369 filed May 30, 2014, the entire contents of which are incorporated herein by reference and this application claims priority to U.S. Provisional Patent Application No. 61/829,801, filed May 31, 2013, which is hereby incorporated herein by reference in its entirety.

TECHNICAL FIELD

The field of embodiments of this invention relates ultra-wideband (UWB) radar, and more particularly to UWB radar systems for non-invasive, real-time detection and tracking of tumors.

BACKGROUND

Lung cancer is the second leading cause of new cancer cases in North America, accounting for 14% of all cancer cases in both men and women. The current five-year survival rate for lung cancer is only 16%. Radiation therapy for the treatment of cancer makes use of preoperative data such as magnetic resonance imaging (MRI), x-ray computed tomography (CT), or positron emission tomography (PET) data to determine the location of tumors to be irradiated. However, many cancerous tumors move during radiation therapy. For example, lung cancer tumors can be particularly problematic due to the type of tissue as well as the fact that the patient is breathing, thus resulting in motion of the patient's lungs. Thus, a major challenge in radiotherapy of lung cancer is to account for tumor motion associated with respiration. A treatment margin must be added to accommodate the range of tumor motion. As a result, radiation damage to normal tissues within the margin is inevitable and limits the tumorcidal dose that can be delivered. The above-noted imaging modalities are not practical to be used in real time during radiation therapy so errors in the actual location of tumors can be quite large.

A solution to the problem has sought to deliver radiation dose to the tumor when it is at a particular anatomic location so that a smaller beam aperture can be used. Currently, two clinical techniques of motion management are employed: (1) In respiratory gating, the beam is turned on only when the tumor is at a certain position during the respiratory cycle, typically at the quiescence period near the end of exhalation; and (2) In active breathing control, breath-hold is applied with a valve to immobilize the tumor for irradiation at a pre-determined lung volume during deep inspiration. Both approaches would require some form of imaging to monitor the tumor position. Unfortunately, all current monitoring methods are sub-optimal, most of them employ x-ray imaging of implanted markers which impart undesirable additional dose and involve an invasive procedure. Other methods employ external surrogates with some degree of uncertain validity. Furthermore, ultrasound imaging, although it can provide real time imaging of some tumors, generally requires direct contact with the patient and usually by an operator with a hand-held ultrasound probe. In addition, ultrasound is not useful for lung cancer since the chest and particularly the lungs are not good media for ultrasound wave propagation. Thus, ultrasound cannot penetrate through lung tissues. Therefore, treatment of lung tumor patients is difficult as the imaging is equivalent to "shooting" in the dark. In addition to the disadvantages discussed above, MRI and CT are difficult to operate simultaneously with medical linear accelerators. Consequently, it also is not practical for providing real-time tumor locations during radiation therapy. Furthermore, imaging modalities such as CT and PET, for example, use ionizing radiation which imposes its own health concerns.

Ultra-Wide Band (UWB) radar transmits and receives a radio-frequency pulse of ultra-wideband frequencies encompassing from 3.1 to 10.6 GHz. UWB technology is relatively new in medical physics but is very well known in the radar world as a "through-the-wall" technology. There have been many publications on detecting humans and vehicles through walls of concrete and ground penetrating radar being used to find hidden features. See e.g., Nguyen et al., "Computerized tomographic radar target imaging behind opaque walls," Optical Engineering 46(7), 076201 (2007); Dogaru et al., "SAR images of rooms and buildings based on FDTD computer models," IEEE Trans. Geosci. Remote Sensing 47(5), 1388-1401 (2009); Schechter et al., "High-resolution 3-D imaging of objects through walls," Optical Engineering 49(11), 113204 (2010); and Sukhvinder S et al., "Sense through wall human detection using UWB radar," EURASIP Journal on Wireless Communications and Networking 20(1), (2011). Historically, the UWB was restricted to military use until the Federal Communications Commission (FCC) released these bandwidths for commercial usage in 2002. Since then UWB technology has been rapidly developing in government and commercial applications for imaging and communications. Examples of applications are "through-the-wall" imaging to detect the location of static or moving objects behind the wall, ground-penetrating radar to find objects buried under ground (Park et al., "Development of a UWB GPR system for detecting small objects buried under ground," IEEE Conference proceedings of Ultra WideBand Systems and Technologies 384-388 (2003)), surveillance (see Immoreev et al., "Ultra-wideband radar for remote detection and measurement of parameters of the moving objects on small range," *Conference proceedings of Ultra Wideband and Ultra Short Impulse Signals* pp 1-3 (2004)), and search and rescue of people trapped under collapsed buildings. Medical applications include remotely monitoring patient's vital signs (see Immoreev et al., "UWB radar for patient monitoring," *IEEE A&E Systems Magazine* pp 11-18 (2008); Staderini et al., "UWB Radars in Medicine," *IEEE AESS Systems Magazine* pp 13-18 (2002); Paulson et al., "Ultra-wideband radar methods and techniques of medical sensing and imaging," *Conference proceedings of SPIE International Symposium on Optics East*, Boston, Mass., UCRL-CONF-216016 (2005); and Thiel et al., "Ultra-wideband sensors for improved magnetic resonance imaging, cardiovascular monitoring, and tumor diagnostics," *Sensors* 10(12), 10778-10802 (2010)), obstetrics imaging, hemorrhage detection in the brain, involuntary head-motion sensors for MRI, and breast tumor detection (Li et al., "Microwave imaging via space-time beamforming: Experimental investigation of tumor detection in multilayer breast phantoms," *IEEE Trans. Microw. Theory Tech.*, 52(8), 1856-1865 (2004); Winters et al., "Three-dimensional microwave breast imaging: Dispersive dielectric properties estimation using patient-specific basis functions," *IEEE Transactions on Medical Imaging*, 28(7), 969-981 (2009); and Klemm et al., "Towards contrast enhanced breast imaging using ultra-wide band microwave radar system," *IEEE Radio and Wireless Symposium*, pp 516-519 (2010)). UWB nano-pulse radar has multiple advantages over many existing technologies currently used in the medical industry. It is non-ionizing, non-invasive, non-contact, low cost, and can produce results in real-time. It is also capable of penetration through lung tissue to directly detect tumors while treatment is being applied and it does not interfere with existing radiotherapy systems. UWB radar has been employed to monitor vital cardiac and respiratory vital signs. Since UWB is non-ionizing and non-invasive, it can be used for long-term and frequent imaging for cancer patients. However, a UWB radar system for real-time monitoring of 3D lung-tumor position during radiotherapy has not been developed. Thus, the need for non-invasive, non-ionizing, non-contact, and real-time technique to detect lung-tumor position during radiotherapy has been an elusive feat.

Therefore, there remains a need for improved systems and methods for non-invasive, real-time detection and tracking of tumors.

SUMMARY

In one embodiment, an ultra-wideband (UWB) radar system for non-invasive, real-time tumor tracking includes an UWB transmitter arranged to transmit radar pulses to penetrate a region of interest of a patient; an UWB receiver arranged to receive radar return pulses after being reflected by tumor tissue in the region of interest of the patient; and an UWB signal processor constructed to communicate with the UWB receiver, wherein the UWB transmitter and the UWB receiver are constructed to be arranged sufficiently far away from the patient so as to avoid interfering with radiation treatment of the tumor.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "real time" as used herein is intended to mean a time period sufficiently short to be useful during a medical treatment and/or procedure that depends on knowledge of the location of a tumor.

Figure 1A:
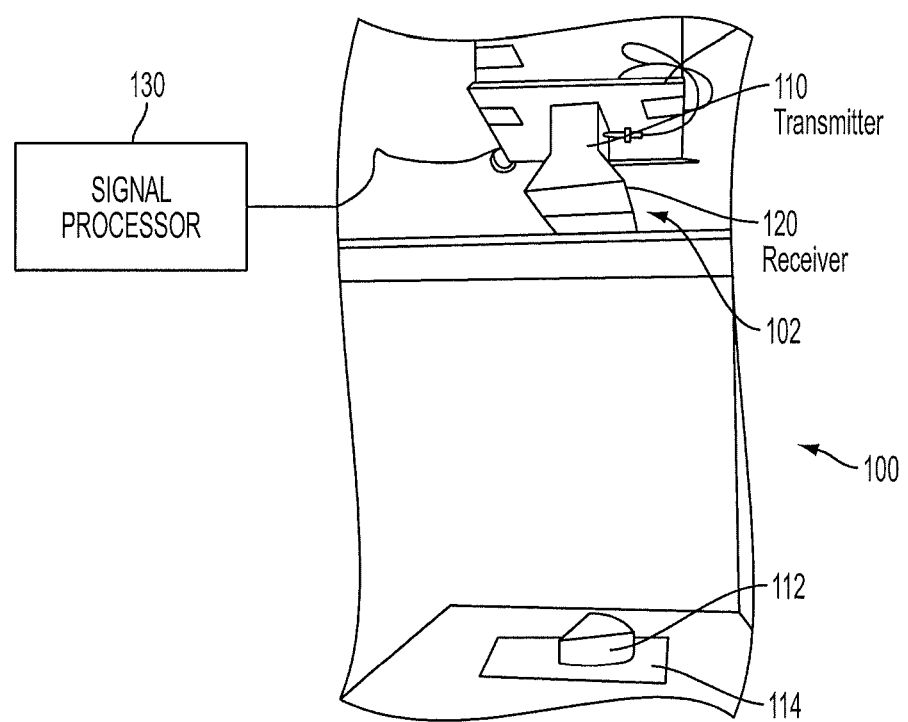
FIGS. 1A and 1C show an embodiment of a UWB radar system placed vertically, looking down from a ceiling.

FIG. 1A is an illustration of an UWB radar system 100 for non-invasive, real-time tumor tracking according to an embodiment of the current invention. In FIG. 1A, the UWB radar system 100 for non-invasive, real-time tumor tracking, includes an UWB transmitter 110 arranged to transmit radar pulses to penetrate a region of interest of a patient; an UWB receiver 120 arranged to receive radar return pulses after being reflected by tumor tissue in said region of interest of said patient; and an UWB signal processor 130 constructed to communicate with the UWB receiver 120, where the UWB transmitter 110 and the UWB receiver 120 are constructed to be arranged sufficiently far away from the patient so as to avoid interfering with radiation treatment of the tumor.

The UWB radar system 100 includes an UWB transmitter 110 arranged to transmit radar pulses to penetrate a region of interest of a patient, an UWB receiver 120 arranged to receive radar return pulses after being reflected by tumor tissue in the region of interest of the patient, and an UWB signal processor 130 constructed to communicate with the UWB receiver 120. The UWB radar system 100 can be used to generate electromagnetic pulses with nanosecond width encompassing frequencies of about 3-10 GHz. The radar can consist of radio-frequency pulses around a nanosecond in duration encompassing the frequencies of about 3.1 GHz to about 10.6 GHz. This radar consists of radio-frequency pulses around a nanosecond in duration encompassing the frequencies 3.1 GHz to 10.6 GHz. By measuring the time-of-flight of the pulse between transmission and reception, the UWB radar system 100 can precisely track the position of an object.

The UWB transmitter 110 and UWB receiver 120 can be set up vertically and pointing down as shown in FIG. 1A. The UWB transmitter 110 and the UWB receiver 120 can each include a horn antenna 102 to provided directional transmission and detection of radar pulses. The UWB radar system 100 generating short pulses can have an omni-directional antennae element. In describing UWB as body penetrating radar, a first step can include focusing UWB signal with a horn-antenna. Uni-directional antennae can focus beam power and detect objects in free space. The horn-antenna is a waveguide that is custom made for the specific frequency(ies) of operation. A horn-antenna is an antenna that consists of a flaring-metal waveguide shaped like a horn to direct radio waves in a beam. Waveguide theory can be used in designing the horn-antenna. By applying waveguide theory, a horn-antenna and its waveguide can be custom designed for the specific frequencies of operation. The omni-directional beam can be changed to a uni-directional beam by placing the element inside a horn-antennae. By designing a horn-antenna with an aluminum inner lining, using waveguide theory, skin depth of the aluminum, cut off frequencies at lower frequency, radiating element size, and horn gain, can be taken into consideration.

The UWB transmitter 110 and the UWB receiver 120 are constructed to be arranged sufficiently far away from the patient so as to avoid interfering with radiation treatment of the tumor. By measuring the time-of-flight of the pulse between transmission and reception, the UWB radar system 100 can precisely track the position of an object. Since UWB is not a single frequency, but rather contains collection of frequencies (3-5 GHz in one embodiment) in a pulsed signal, resolution is not limited by a single wavelength but rather rely on time-of-arrival of leading edge technique. Thus, according to one embodiment of the current invention, a collection of frequencies from 3-5 GHz can be used. For example, as shown in FIG. 1C, the UWB transmitter 110 and the UWB receiver 120 can be mounted on a surface that is about 66 cm from a target of a tissue sample.

Figure 1B:
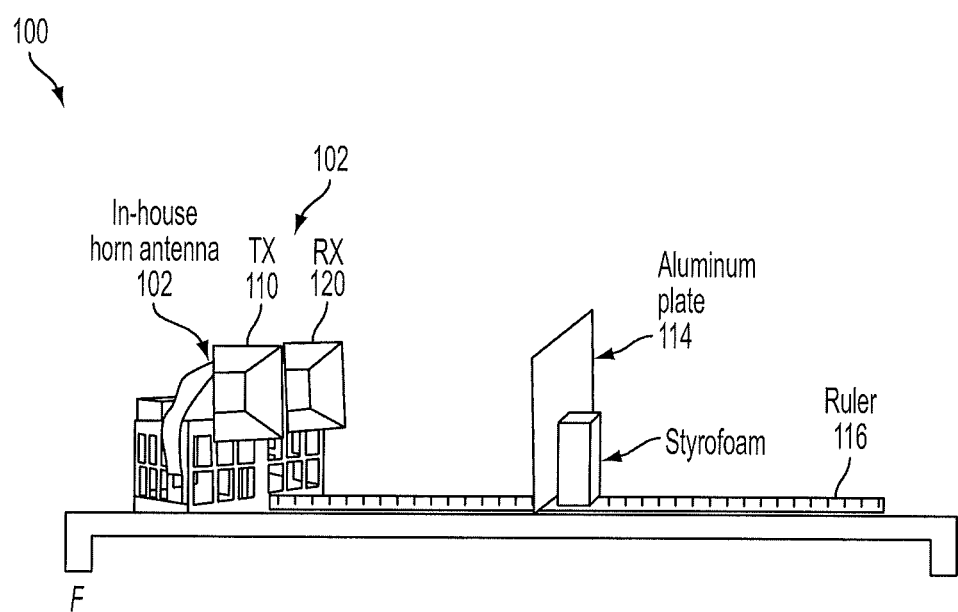
FIG. 1B shows an embodiment of a sideways UWB radar system in relation to a ruler.
Figure 1C:
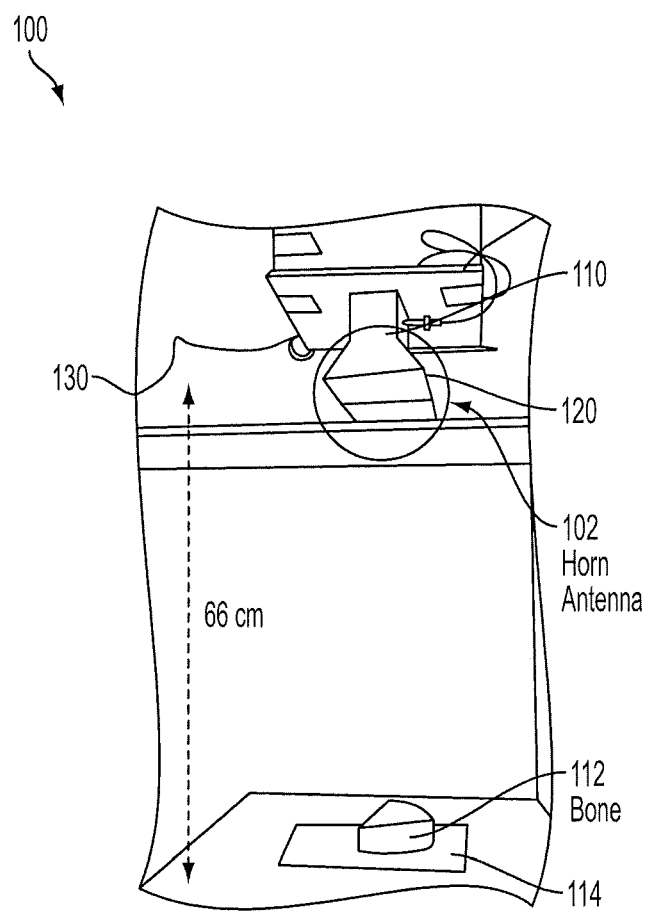
Figure 2:
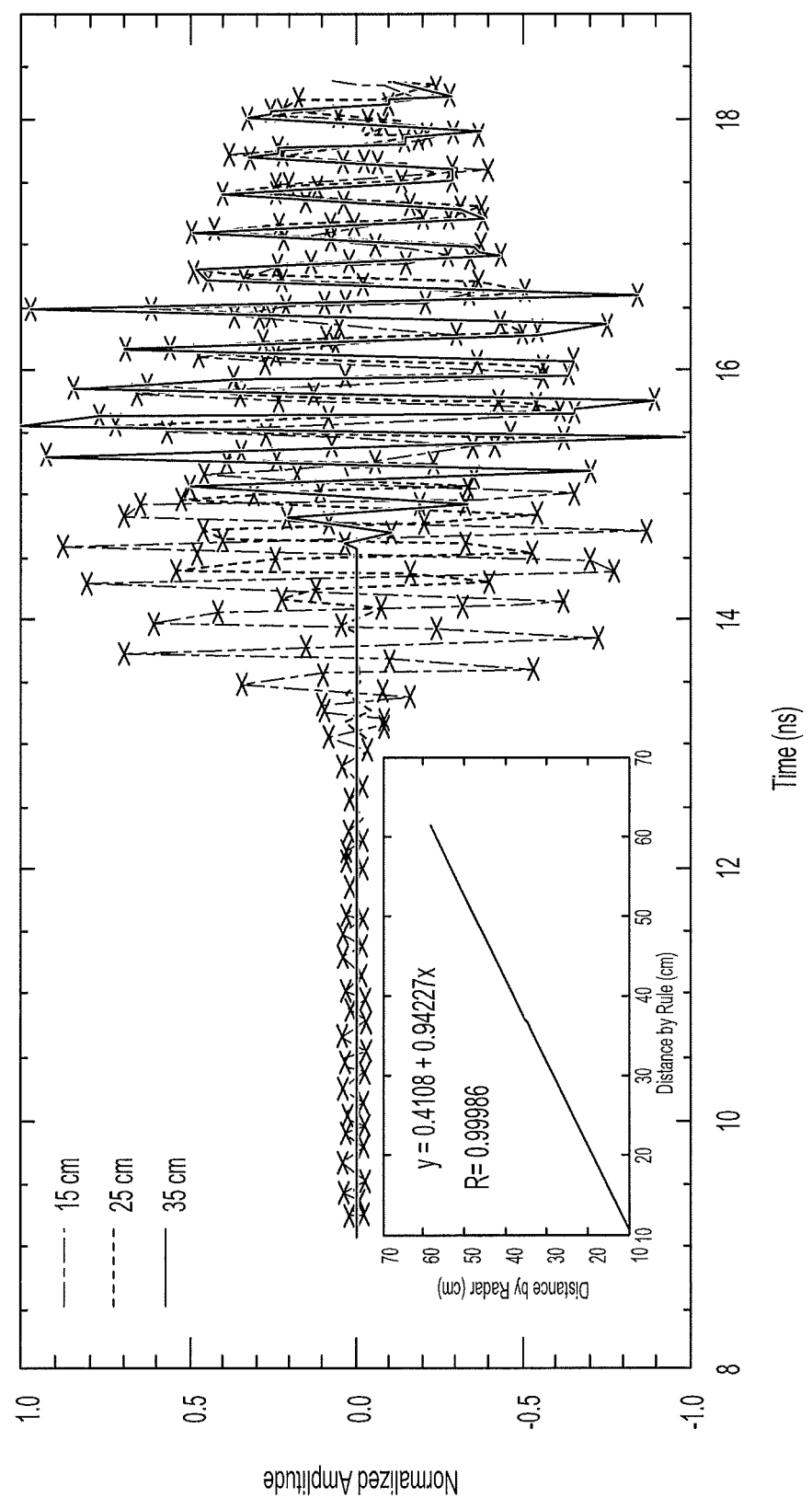
FIG. 2 shows time-of-arrival of reflected pulse. The inset of FIG. 2 shows a comparison of the radiometric distance to a physical distance.

Target-position can be calibrated, as shown in FIG. 1B. For example, an aluminum plate 114, much smaller than the sample tissue, can be placed underneath the tissue sample. For the target-position calibration, a position of the aluminum plate, which was moved in 1-cm increments away from the UWB transmitter 110 and the UWB receiver 120, can be measured using, for example, a ruler 116. Measurements can be subtracted to extract only the reflected signal from the aluminum plate through the tissue to the UWB receiver 120. A purpose of the measurement can be to extract only the reflected signal from the aluminum plate 114 under the tissue sample 112 and remove other extraneous signals from the measurement, which can be referred to as the background subtracted signal. An increase in the aluminum plate distance can delay the time-of-arrival of the leading-edge of the pulse to the UWB receiver 120. A leading edge can also be extracted as a position of the plate, as shown in the inset of FIG. 2. As shown in FIG. 2, a radiometric distance measured from the leading edge of the radar signal can agree very well with the physically measured distance. At a sampling rate of 16.7 GHz, a spatial resolution of 0.91 cm can be obtained. With a sampling rate of 500 GHz, the spatial resolution can be improved up to 0.03 cm.

An embodiment of the current invention adapts UWB technology for lung tumor detection in real-time. Unlike ultrasound, UWB can penetrate through air. A horn antenna 102 can be built using cut off frequency 2.14 GHz with waveguide dimension 7×7×7 cm and flare out distance R=14 cm. After successful construction, angular energy distribution can be measured in both H-plane and E-plane. Spatial resolution is measured by targeting an aluminum plate (3.3 cm×2.4 cm) which is moved with 1-cm increment. To ascertain the position, a leading-edge time-of-arrival detection technique can be used. The UWB radar system 100 can detect a small size object such as gold fiducials with a high SNR. Also, small gold fiducials (0.1 cm×1 cm) can be targeted for position detection. The spatial resolution of one embodiment can be 0.915 cm. However, with modification, spatial resolution can be improved to 0.03 cm. The gold fiducials are detected with SNR=8. 18.5±° 31.4+°. Thus, a uni-directional horn-antenna using waveguide theory and characterized angular beam width and spatial resolution can be built according to an embodiment of the current invention to focus a smaller beam.

Figure 5B:
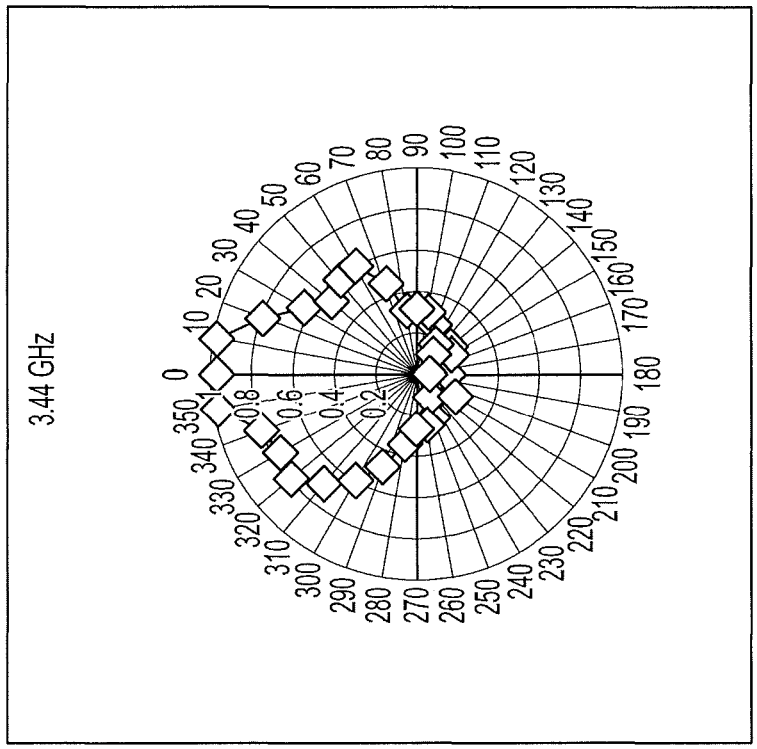
FIG. 5A shows measuring angular energy distribution in H-plane and FIG. 5B shows measuring angular energy distribution in E-plane.
Figure 5A:
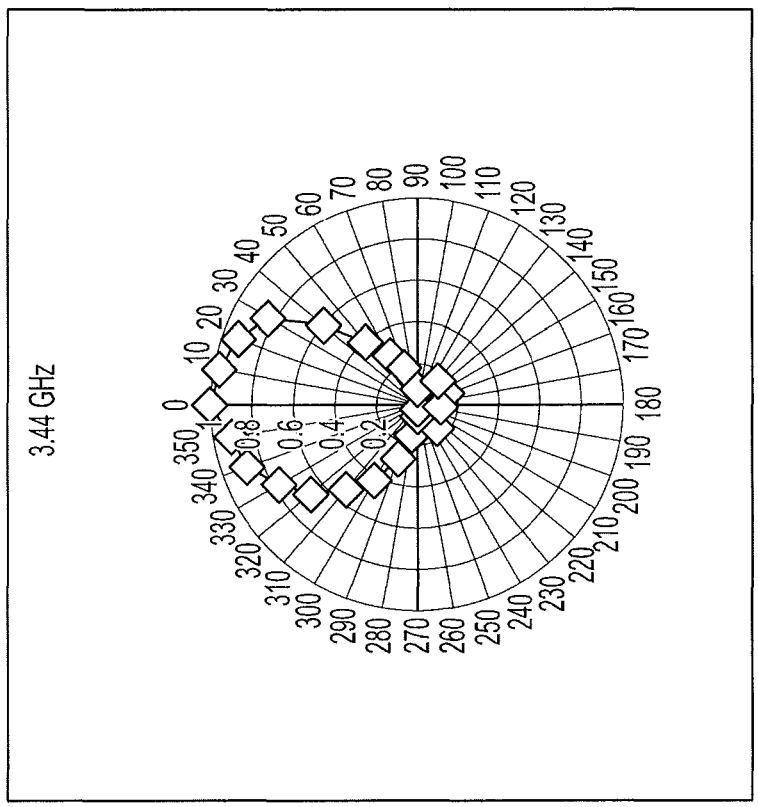

In FIG. 5A, a radar plot for H-plane and in FIG. 5B, a radar plot is shown for E-plane for central frequency 3.44 GHz. A directional horn-antenna can have beam widths containing greater than 50% energy within +/−18.5° for H-plane, and +/−31.4° for E-plane at 3.5 GHz for the central frequency of 3.44 GHz. Using UWB nano-pulse radar, a tumor position can be directly detected with a spatial resolution of 0.03 cm and the frame rate of greater than 40 Hz. The uni-directional horn-antennae according to an embodiment of the current invention can have beam widths containing >50% energy within for H-plane, and for E-plane at 3.5 GHz. Using this, distance measurement of an aluminum plate which is moved in 1 cm increment can be performed. This increase in distance changes the time-of-arrival to the receiver and its leading edge is detected and plotted in the inset of FIG. 2.

An embodiment of the current invention includes an UWB radar system 100 with customized horn antennae 102 where a UWB pulse can penetrate through biological tissues and reflect back with useful information. A non-ionizing imaging technique can impact a radiation treatment by increasing accuracy of radiation delivery based on real-time tumor information. In radar theory, penetration into biological tissues is a function of refractive index n. From this, one can calculate transmission and reflection coefficients. Biological tissues are characterized by complex permittivity $\bar{\varepsilon}=\varepsilon'-i\varepsilon''$ and is related to complex refractive index $\bar{n}=n-i\kappa$.

We have that $$n = \sqrt{\frac{\sqrt{\varepsilon_1^2 + \varepsilon_2^2} + \varepsilon_1^2}{2}}$$

and $$\kappa = \sqrt{\frac{\sqrt{\varepsilon_1^2 + \varepsilon_2^2} + \varepsilon_1^2}{2}}.$$

For reflection and transmission coefficients, we get $$b^2 = \frac{1}{2}\left\{\sqrt{[(n^2-k^2)^2 + 4n^2k^2]} - (n^2-k^2)\right\}.$$

How much power can penetrate into biological tissue is governed by $P=P_0 e^{-2\alpha z}$ where $$\alpha = \frac{2\pi}{\lambda_0}\left[\frac{1}{2}\left(\sqrt{1+\left(\frac{\varepsilon''}{\varepsilon'}\right)} - 1\right)\right]^{1/2}$$

where $\lambda_0$ is wavelength in free space. Often in radar realm, we calculate depth at which the power attenuates 1/e from the surface. This is given as $$dp = c/2\pi \sqrt{2\varepsilon'\left(\sqrt{1+\left(\frac{\varepsilon''}{\varepsilon'}\right)} - 1\right)}.$$

Using the above equations, numerical simulations for human tissues such as skin, fat, muscle, bone, and lung can be performed to determine penetration of UWB signals (3-5 GHz). Permittivity values from a published source can be used. For example, an experimentally measured complex permittivity can be extracted and input to the model. $'\varepsilon$ "$\varepsilon$ Published values for (1/e) penetration depth are disclosed in Gabriel et. al., "The dielectric properties of biological tissues: I. Literature survey," Phys. Med. Biol. 41 (1996) 2231-2249; Gabriel et. al., "The dielectric properties of biological tissues: II. Measurements in the frequency range 10 Hz to 20 GHz," Phys. Med. Biol. 41 (1996) 2251-2269; and Gabriel et. al., "The dielectric properties of biological tissues: III. Parametric models for the dielectric spectrum of tissues," Phys. Med. Biol. 41 (1996) 2271-2293, the content of which is hereby incorporated herein by reference in its entirety. (1/e) penetration depth is equivalent to 36.7% of the initial radar power, for human skin, muscle, fat, bone, and lung to be 4.45, 4.66, 0.45, 2.60, and 2.38 cm, respectively, for 4 GHz central frequency. This result can be used to design an experiment for further investigation. $'\varepsilon$ "$\varepsilon$ An aspect in this investigation is that UWB is able to penetrate through all levels of tissues including the lung tissue. Transmission/reflection coefficients of tumors can also be calculated and the positions can be detected accordingly. In the case of lung cancer, the tumors are expected to interact with the UWB signals in a way more similar to water than that of the lung tissue. UWB pulsed signal can penetrate through biological tissues such as human skin, muscle, bone, fat, and lung. Complex permittivity can be related with complex index of refraction to obtain reflection and transmission coefficients for skin, muscle, bone, fat, and lung and ascertain the amount of power that can be transmitted and reflected. Thus, penetration distances, transmission, and reflection power (normalized) can be calculated for various samples. With enough signal power and fast sampling rate, a tumor's exact position can be extracted via non-contact, non-ionizing, and non-invasive radar technique.

THE UWB radar system 100 can further include a dielectric lens 138 arranged between the horn antenna 102 of the UWB transmitter 110 and the region of interest of the patient to further focus radar pulses thereon. By modifying an omni-directional beam into a uni-directional beam, it allows for focusing and measuring either in the field-of-view, through-the-wall, and through-the-human body. One of the components of UWB radar system 100 according to an embodiment of the current invention can include an aperture stop 134 arranged between the horn antenna 102 of the UWB receiver 120 and the region of interest, in which the aperture stop 134 includes radar absorbing material to block stray radar signals that return from regions other than the region of interest.

Figure 3A:
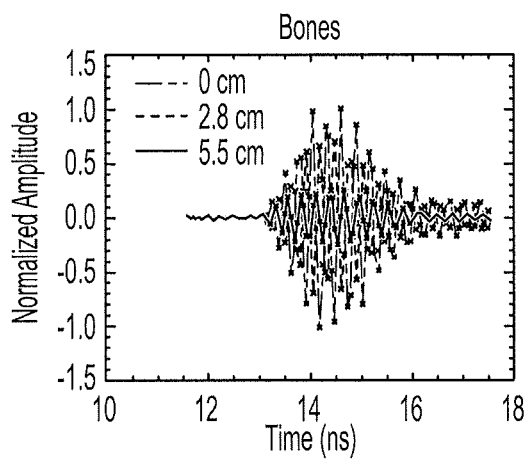
FIG. 3A shows reflected signals with various thicknesses of bones.
Figure 3B:
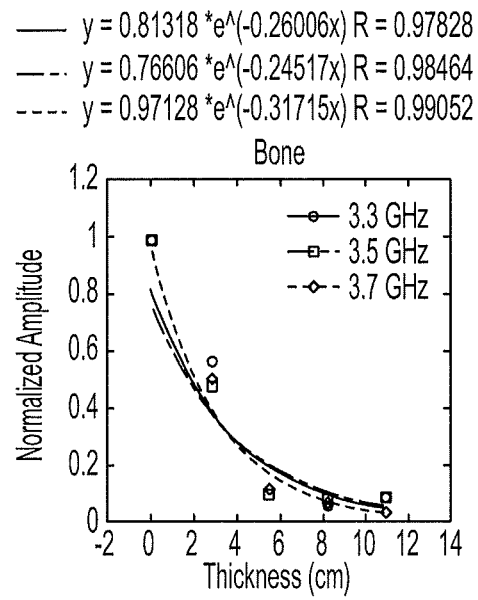
FIG. 3B shows plotted Fourier transformed reflected signals of FIG. 3A.

FIG. 3A shows reflected signals with various thicknesses of bones being increased by ½ inch (approximate). Each oscillating signal is background-subtracted signal showing only the reflected echo from the aluminum plate under the bone. The echo signal was Fourier transformed, and amplitude of the three central frequencies was plotted as a function of bone thickness, as shown in FIG. 3B. The amplitude was fitted with an exponential decay function (fitting accuracy >97.8% for all three frequencies), and the thickness of the 1/e (36.7%) transmission depth was calculated for the bone. The biological tissues exhibit different signal attenuation. The tissue such as pig skins has much greater attenuation than bones. Thus, UWB signal can penetrate through biological tissues.

Figure 4:
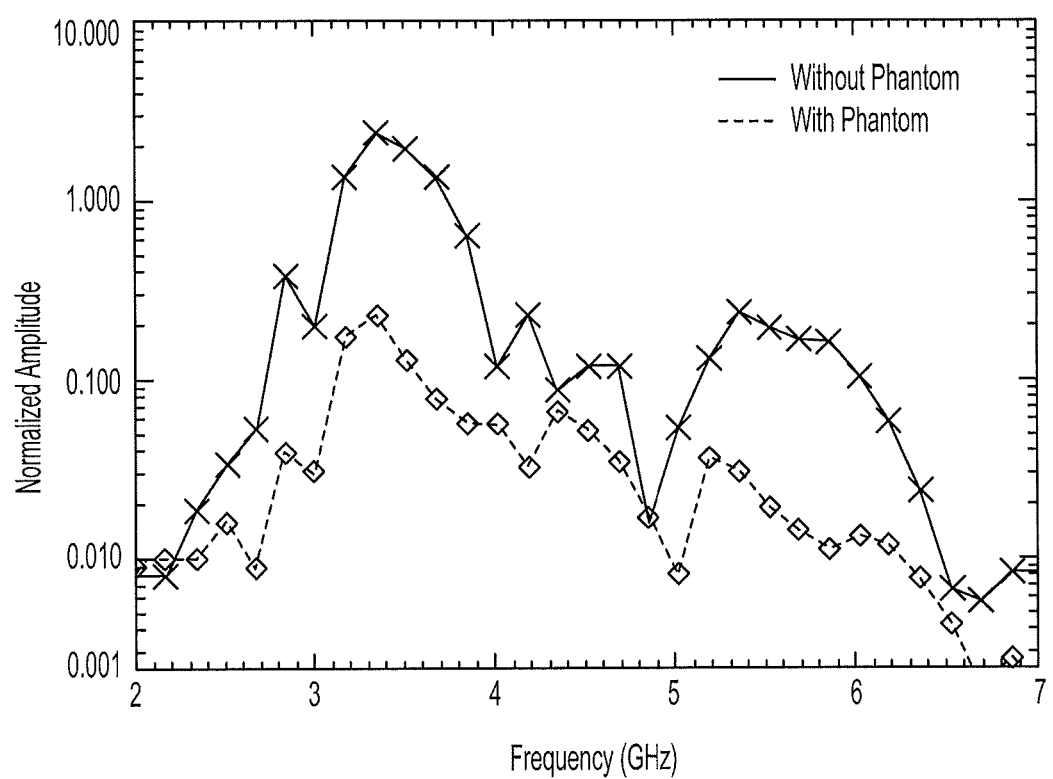
FIG. 4 shows Fourier-transformed reflected signals from a water balloon.

Additionally, a phantom consisting of 0.2-cm skin, 2.0-cm fat, 0.5-cm muscles, and 2.4-cm wet sponge stacked in series can be used as a miniature version of a human thorax. Instead of an aluminum plate, a 20-ml water-filled balloon (diameter ~5 cm) can be placed under the phantom to mimic lung tumor. FIG. 4 shows Fourier-transformed reflected signals from the water balloon. The top line (with Xs) is the reflected signal from the balloon without the miniature phantom and the bottom line (with diamonds) is the signal with the phantom. For the miniature phantom described, a water-filled balloon of approximately 5 cm under layers of tissues were detected as shown in FIG. 4. Two plots represent echo signals reflected only from the balloon with (Xs) and without (diamonds) the phantom. Thus, the echo signal can be attenuated by the phantom, but can detect the balloon mimicking a lung tumor.

The UWB transmitter 110 can be configured to transmit radar pulses that have an electromagnetic frequency within the range of 3 GHz to 10 GHz. The UWB transmitter 110 can be configured to transmit radar pulses that have an electromagnetic frequency within the range of 3 GHz to 5 GHz. The UWB transmitter 110 can be configured to transmit radar pulses that have pulse widths of about 100 picoseconds to about 1 nano-second.

The UWB signal processor 130 can be configured to perform leading edge detection with a return-distance resolution of less than about 2 cm. The UWB signal processor 130 can be configured to perform leading edge detection with a return-distance resolution of less than about 0.5 cm. The UWB signal processor 130 can be configured to perform leading edge detection with a return-distance resolution of between about 1 mm to about 5 mm.

The UWB signal processor 130 can be configured to detect a position of the tumor in real time and communicate with a radiation treatment control system. At least one of the UWB transmitter 110 and the UWB receiver 120 can be arrays of transmitters or receivers, respectively. Thus, the UWB radar system 100 can be used as a real-time monitoring of cancer or tumors without interfering with treatment beam delivery. Since UWB can easily penetrate through air with almost zero attenuation, it can monitor lung-tumor motion remotely in real time.

In addition, the UWB radar system 100 may be upgraded to a higher power generation from −14.5 to 0.7 dBm. Since the double-ridge horn antennae can have high efficiency/gain and low voltage-standing-wave-ratio (VSWR), power can radiate directionally with a minimal power loss to reach deep-seated lung tumors. A UWB radar system specifically built for the tumor-position detection can be characterized in terms of radiating-beam width and power, electronic noise level, and temporal/spatial resolutions. The experiments described in FIG. 1B and FIG. 2 can be repeated for this step.

Figure 6:
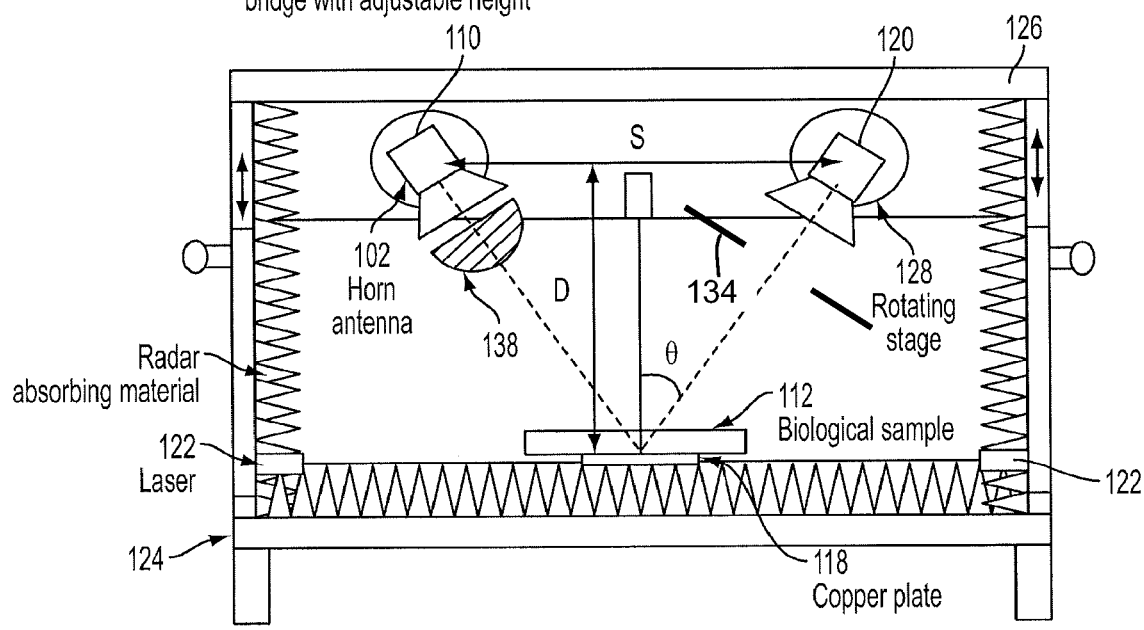
FIG. 6 shows a UWB radar system having a C-shaped bridge.

In one embodiment, commercial double-ridge horn antennae with a dielectric lens 138 may be used, which can provide a radiating-beam width covering only the region of interest for tumor tracking, as shown in FIG. 6. See Gabriel et al. *The dielectric properties of biological tissues: I. Literature survey* Phys. Med. Biol. 41(11) 2231-2249. FIG. 6 shows that the UWB radar system 100 can include a bridge 124 that is a standalone structure and can be easily moved to a different location. The bridge 124 can be C-shaped in one embodiment. A mounting panel 126 extended from the top of the bridge can adjust separation distance, S, between the UWB transmitter 110 and the UWB receiver 120. Rotating stages 128 and a height-adjustable C-shaped bridge will add the capability to change the angle, θ between the UWB transmitter 110 and the UWB receiver 120 and distance, D, from the antennae and the target. The bridge will be covered by radar absorbing material to minimize extraneous reflections from it. A bench can be detached when the UWB radar system 100 is used with a treatment couch. Lasers 122 mounted on the top and both sides of the bridge 124 will be used to localize the target location at a distance, D, from the antennae 102. Repeating the experiments shown in FIG. 4, system setup parameters, S, θ and D can be configured by iterative measurements of the reflected signals from at least one copper plate 118 in air and under human tissues. The at least one copper plate 118 can reflect the electromagnetic signal with a minimal loss.

Figure 7:
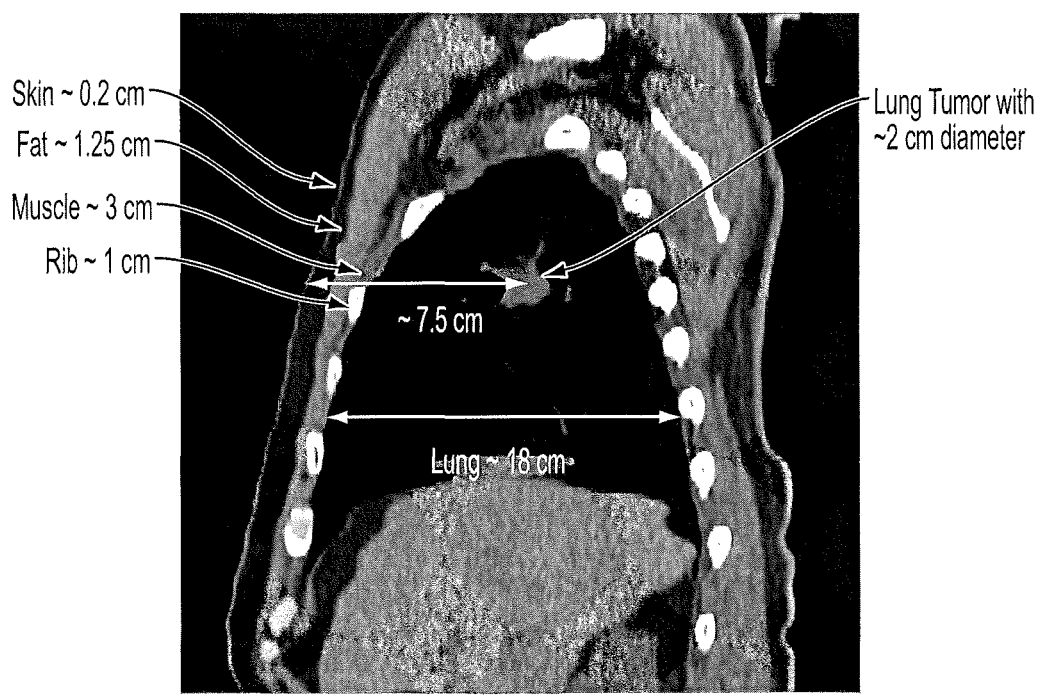
FIG. 7 shows an example of a solitary lung tumor.

FIG. 7 shows an example of a solitary lung tumor that is ~2 cm in diameter, located approximately 7.5 cm from the chest underneath ~0.2 cm of skin, ~1.25 cm fat, ~3 cm muscle, and ~6.5 cm normal lung tissue. Tumors can be inherently irregular in shapes. Size, location and motion of lung tumors will vary with patients. Respiration and the associated tumor motion are cyclical with an average period of 4 seconds, ranging from 2.5 to 7 seconds. Lung tumor moves predominantly in the superior-inferior (SI), along the feet-to-head axis, and less so in the anterior-posterior (AP), i.e. front-to-back and left-right (LR) directions. Motion management is typically applied in the radiation treatment of lung tumors that are 1 cm or larger in diameter, and which move more than 5 mm with respiration. Pertinent to the application of UWB radar for the detection of lung tumor motion is the dielectric properties of various human tissues. Dielectric properties of human tissues at 4 GHz can be shown in Table 1.

TABLE 1

Dielectric properties of human tissues at 4 GHz.

| Medium | $(\sigma/\omega\varepsilon_r)^2$ | $\varepsilon_r$ |
|---|---|---|
| Air | 0.00 | 1.00 |
| Fat | 0.04 | 5.50 |
| Muscle | 0.10 | 50 |
| Cartilage | 0.15 | 35 |
| Lung | 0.11 | 20 |
| Heart | 0.11 | 55 |

In stereotactic radiosurgery of lung tumor, a desirable margin for tumor motion can be less than 5 mm, and preferably about 3 mm. Given the resolution of most imaging modalities employed in radiation therapy, a 3D lung-tumor position (SI, AP, LR) can be detected with a spatial accuracy of 1 mm and a temporal accuracy of 100 ms. In one embodiment, multiple sensors may be employed. The 3D position of the moving tumor can be represented by the position of its surface or its center of mass. Consistency of the representative signal can be important that infer 3D information, such as shape or selected surface features. The application of UWB radar for motion management in radiation therapy can involve evolving phases of hardware and software developments.

Figure 8:
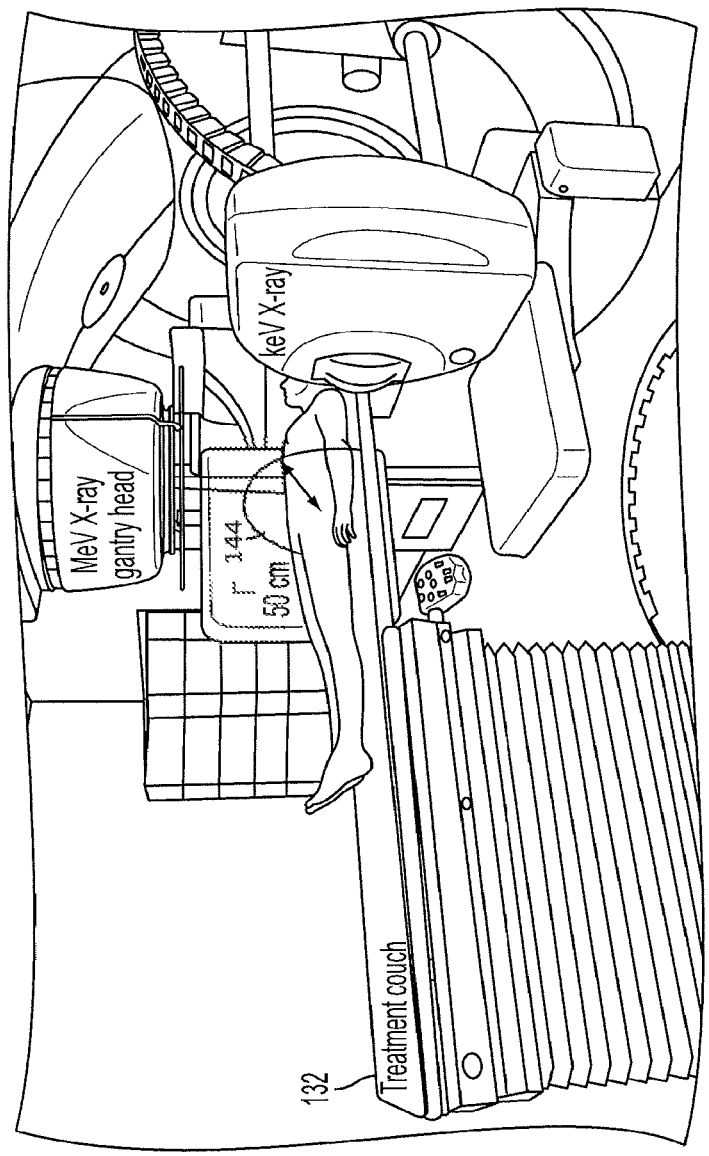
FIG. 8 shows a treatment room for radiotherapy with a linear accelerator gantry head generating megavoltage (MV) x-rays as an example for deploying the UWB radar system 100.

FIG. 8 shows a treatment room for radiotherapy with a linear accelerator gantry head generating megavoltage (MV) x-rays to treat tumors as an example for deploying the UWB radar system 100. A patient can lie down on a treatment couch 132 made of carbon fiber. A kilovoltage imaging system consisting of a diagnostic kVp x-ray tube and a flat-panel detector produce projection images or 3D cone-beam CT images for setting up the patient for treatment. The UWB radar system 100 may be placed in a circular array at a radius of 50 cm, shown as the semicircle 144 in FIG. 8, from the isocenter (the intersection point of rotation axis of MV gantry head, treatment couch, and kVp x-ray head). For any deployment strategy, interference with the radiation beam or influence of the UWB radar signals due to the treatment room environment must be considered.

Without limiting the invention from the broad inventive principles disclosed herein, some examples are presented. A goal of some experiments is to answer some questions: 1) Can UWB penetrate through biological tissues? 2) Can UWB detect tumor like material inside the body? 3) Can UWB be used to promote development of non-contact, non-invasive, non-ionizing, and real-time radar system for tumor detection? With the results presented here, all three questions have been answered yes.

To experimentally demonstrate UWB penetration, a series of two complementary measurements were performed: 1) tissue sample with aluminum plate behind, and 2) tissue only. The two measurements were subtracted to isolate only the reflected echo signal through the tissue. To mimic human tissues, pig skins, cow muscles, bones, fat, and wet-sponges (lung) were used. Additionally, a phantom consisting of 0.2-cm thick skin, 2.0-cm fat, 0.5-cm muscle, and 2.4-cm wet sponge was used as a miniature version of a human thorax. A 20-ml water balloon (22.0 g, diameter: ~5 cm) was placed under the phantom as a lung tumor. The echo signal reflected from the water balloon was measured. UWB can penetrate through all biological tissues with varying transmission. Specifically, the 1/e (36.7%) transmission depth from air to bone, fat, skin, muscle, and wet sponges are 3.03 cm, 2.47 cm, 0.19 cm, 0.49 cm, and 3.47 cm, respectively. The penetration depth can be increased by optimizing the UWB radar system 100 with a higher power. In the phantom-tumor experiment, the echo signal from the water balloon was detected with a signal-to-noise ratio of ~2 and its amplitude was reduced to 11.1% compared to the echo signal measured in air without the phantom, as shown in FIG. 4.

To mimic human tissues, pig skins, cow muscles, bones, fat, and wet-sponges (lung substitute) were used as samples. Additionally, a phantom consisting of 0.2-cm skin, 2.0-cm fat, 0.5-cm muscles, and 2.4-cm wet sponge stacked in series was used as a miniature version of a human thorax. Instead of an aluminum plate, a 20-ml water-filled balloon (diameter ~5 cm) was placed under the phantom to mimic lung tumor.

Samples of various biological tissues, such as pig skins, cow muscles, bones, fat, and wet-sponges (lung), were used with a different thickness to mimic human tissues. The samples were placed at a distance of 66 cm from the tip of the UWB transmitter 110 of the horn antenna 102. A platform on which the samples are placed are made with a rigid cardboard without any metal components in the field of view of the UWB transmitter 110/UWB receiver 120. This is to ensure that highly reflective metal do not contribute to our results. Underneath the sample is an aluminum plate no greater than the size of the sample (to avoid energy spill over echo). Two complementary measurements are collected: 1) tissue sample with the aluminum plate, 2) tissue only (background). For 2), the tissue set up when removing the aluminum plate was not disturbed. By background subtraction, 1)-2), the net result is the UWB signal returned to the UWB receiver 120 by echo off from the aluminum plate under the sample. The echo from the aluminum plate which represents penetrated UWB signal through the tissue can be one area of interest to ensure all other extraneous signals to be canceled out.

Figure 3C:
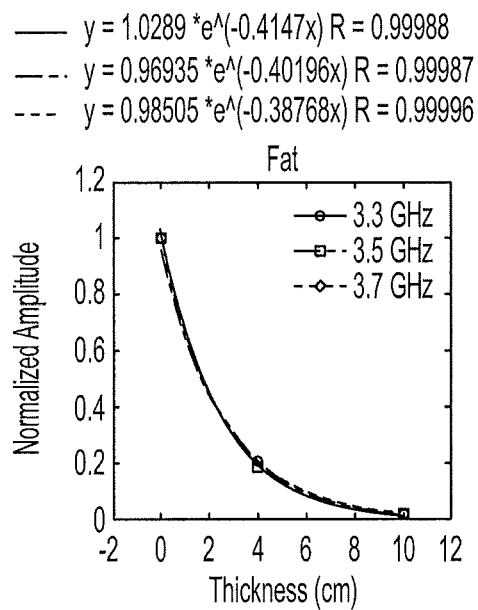
FIG. 3C shows reflected signals of fat that are Fourier-transformed.
Figure 3D:
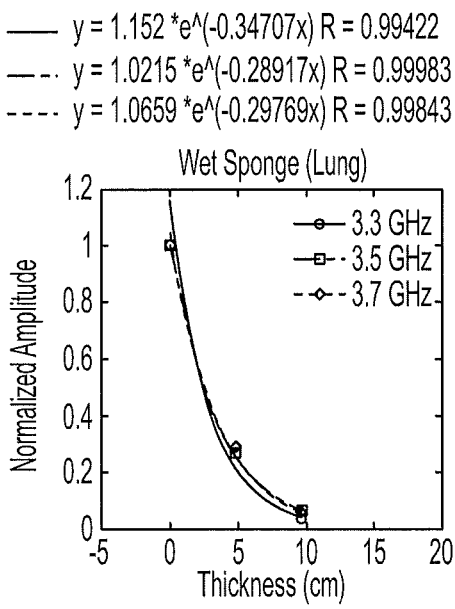
FIG. 3D shows reflected signals from a wet sponge.

Results show that a UWB nanosecond pulse from the radar transmitter 120 was able to penetrate through the biological tissues, reflect off the aluminum plate, and then penetrate back through the tissues to the UWB receiver 120. FIG. 4A shows a background-subtracted signal reflected from the aluminum plate under the various thicknesses of bones. As the thickness of the bones increases, the return signal decreases. This return signal was Fourier transformed and the three main frequencies (3.3, 3.5, 3.7 GHz) were fitted with exponential decay as a function of bone thickness, as shown in FIG. 3B. As for other exemplary biological tissue samples, the results are shown in FIGS. 3C and 3D. Although tissues such as skin and muscles are difficult to penetrate, our experimental results show that the returned pulse is detectable (SNR >1.5) by the UWB receiver 120 for all samples. We conclude that UWB nano-pulse radar can penetrate through all biological tissues with varying transmission and extract the metal plate position under the tissues. Specifically, the 1/e (36.7%) transmission depths from air to bone, fat, skin, muscle, and wet sponge are 1.52 cm, 1.24 cm, 0.09 cm, 0.24 cm, and 1.74 cm, respectively. For the phantom-tumor experiment, the reflected signal from the water balloon was detected with a SNR of −2 as shown in FIG. 4. The preliminary experiment showed that by increasing the transmitting radar power and decreasing the target distance from the antennae, the reflected signal from the deep-seated target can be measured with an increased SNR. The UWB radar system 100 can also be improved by optimizing the angle and distance between the UWB transmitter 110 and the UWB receiver 120. This improved UWB radar system 100 can be expected to be used in future experiments involving cadaver or real human body.

A leading-edge detection algorithm (see Alsindi et al., "Measurement and modeling of ultra wideband TOA-based ranging in indoor multipath environments," *IEEE Transactions on Vehicular Technology*, 58(3), 1046-1058 (2009); Yu et al., "Performance of UWB position estimation based on time-of-arrival measurements," *Proc. IEEE Conf. Ultra wideband Syst. Technol.* (*UWBST*), Kyoto, Japan, pp. 400-404 (2004); and Shimizu et al., "Accuracy of relative distance measurement with ultra wideband system," *Proc. IEEE Conf. Ultra wideband Syst. Technol.* (*UWBST*), Reston, Va., pp. 374-378 (2003)) can be improved and automated to increase the accuracy of a lung-tumor position. A metal ball with 1-cm diameter (small size ball produces low SNR due to low reflection) can be attached to a four-dimensional motion controller and programmed to move sinusoidally in air with various breathing periods (range: 2-10 s) and excursions (range: 3-30 mm) The UWB radar system 100 can measure reflected signals from the moving ball and the leading-edge detection algorithm will be improved to extract the programmed position of the ball. In one embodiment of the UWB radar system, using the time-of-arrival of the pulse, the spatial resolution is limited by the receiver sampling rate of 16.7 GHz which corresponds to 0.91 cm. The updating to a faster sampling rate such as 500 GHz can provide a spatial resolution of up to 0.03 cm. The end product will include demonstration of UWB penetration capability of various human tissues and be able to ascertain position and movement of lung-tumor. With robust antennae on a C-shaped bridge, improvements to the measurement technique can be made and feasibility with better accuracy and deeper penetration of the UWB signal can be investigated.

Using a prototype system with optimal setup parameters, verification that the UWB can penetrate through various tissue layers of human thorax can be obtained. A cadaver can be obtained and a copper plate 118 can be placed under the lung to measure SNR of the reflected signal from the plate. A SNR greater than 1 can be a goal for this step.

Based on the results acquired from the previous steps, a phantom study can be expected to be performed to validate the optimized UWB system for real-time lung-tumor position detection. The lung-tumor sample will be placed under the lung of the cadaver. The lung tumor will be programmed to move in the superior-inferior direction with 4-s breathing period and 2-cm excursion using a four-dimensional motion controller. The lung tumor motion will be measured using the UWB radar system 100 and its position can be extracted as a function of time using our improved leading-edge detection algorithm. The extracted tumor position will be compared to the programmed tumor position to ascertain the accuracy of our UWB system.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An ultra-wideband (UWB) radar system for non-invasive, real-time tumor tracking, comprising:
    an UWB transmitter configured to transmit a plurality of radar pulses to penetrate a region of interest of a patient;
    an UWB receiver configured to receive a plurality of radar return pulses after being reflected by tumor tissue in said region of interest of said patient;
    an UWB signal processor configured to communicate with said UWB receiver; and
    a plate configured to be placed behind the patient so as to reflect the plurality of radar pulses after penetrating the region of interest of the patient,
    wherein said UWB transmitter and said UWB receiver are configured to be arranged sufficiently far away from said patient to avoid interfering with radiation treatment of said tumor tissue, and
    wherein said UWB signal processor is configured to measure a time-of-arrival of a leading edge of one or more radar return pulses in said plurality of radar return pulses, said one or more return pulses having a plurality of frequencies, and to subtract the plurality of radar pulses reflected by the plate after penetrating the region of interest of the patient from the plurality of radar pulses reflected from the region of interest of the patient without the plate, and
    wherein the receiver has a sampling rate of at least 16.3 GHz such that a spatial resolution of less than 0.91 cm is achieved in said tumor tissue, and
    wherein said UWB transmitter and said UWB receiver each comprises a horn antenna configured to provide directional transmission and detection of radar pulses, and
    a dielectric lens arranged between said horn antenna of said UWB transmitter and said region of interest of said patient and configured to further focus radar pulses thereon, and an aperture stop arranged between said horn antenna of said UWB receiver and said region of interest, wherein said aperture stop comprises radar absorbing material configured to block stray radar signals that return from regions other than said region of interest.

2. An UWB radar system according to claim 1, wherein said UWB transmitter transmits radar pulses that have an electromagnetic frequency within the range of 3 GHz to 10 GHz.

3. An UWB radar system according to claim 1, wherein said UWB transmitter transmits radar pulses that have an electromagnetic frequency within the range of 3 GHz to 5 GHz.

4. An UWB radar system according to claim 1, wherein said UWB transmitter transmits radar pulses that have pulse widths of 100 pico-seconds to 1 nano-second.

5. An UWB radar system according to claim 1, wherein said UWB signal processor is configured to perform leading edge detection with a return-distance resolution of less than 2 cm.

6. An UWB radar system according to claim 1, wherein said UWB signal processor is configured to perform leading edge detection with a return-distance resolution of less than 0.5 cm.

7. An UWB radar system according to claim 1, wherein said UWB signal processor is configured to perform leading edge detection with a return-distance resolution of between 1 mm and 5 mm.

8. An UWB radar system according to claim 1, wherein said UWB signal processor is configured to detect a position of said tumor tissue in real time and communicate with a radiation treatment control system.

9. An UWB radar system according to claim 1, wherein at least one of said UWB transmitter and said UWB receiver are arrays of transmitters or receivers, respectively.

10. The UWB radar system according to claim 1, further comprising a rotating stage that is configured to allow for changing an angle between the UWB transmitter and the UWB receiver.

11. The UWB radar system according to claim 1, further comprising a height-adjustable bridge configured to allow for changing a distance between the UWB transmitter and receiver and a target.

12. The UWB radar system according to claim 11, wherein the height-adjustable bridge is C-shaped.

13. The UWB radar system according to claim 11, further comprising a mounting panel that is configured to adjust a separation distance between the bridge and the target.

14. The UWB radar system according to claim 1, wherein the UWB transmitter and the UWB receiver are arranged 66 cm apart.

* * * * *